United States Patent
Gupta et al.

(12) 
(10) Patent No.: US 6,486,317 B1
(45) Date of Patent: Nov. 26, 2002

(54) PROCESS FOR MAKING 2-HYDROXY-4-ALKOXYPHENYL OR 2,4-DIHYDROXYPHENYL SUBSTITUTED 1,3,5-TRIAZINE UV ABSORBERS

(75) Inventors: Ram B. Gupta, Stamford, CT (US); Dennis J. Jakiela, Orange, CT (US); Sampath Venimadhavan, Norwalk, CT (US); Russell C. Cappadona, Norwalk, CT (US); Venkatrao K. Pai, Stamford, CT (US)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 0 days.

(21) Appl. No.: 09/691,502

(22) Filed: Oct. 18, 2000

Related U.S. Application Data

(63) Continuation of application No. 09/388,645, filed on Sep. 2, 1999, now abandoned.
(60) Provisional application No. 60/099,220, filed on Sep. 4, 1998.

(51) Int. Cl.$^7$ ............................................. C07D 251/24
(52) U.S. Cl. ..................................... 544/216; 544/217
(58) Field of Search ................................ 544/216, 217

(56) References Cited

U.S. PATENT DOCUMENTS

| | | | | |
|---|---|---|---|---|
| 3,118,887 A | * | 1/1964 | Hardy et al. ................ | 544/217 |
| 3,242,175 A | | 3/1966 | Duennenberger et al. ... | 260/248 |
| 3,244,708 A | * | 4/1966 | Duennenberger et al. ... | 544/217 |
| 3,249,608 A | | 5/1966 | Biland et al. ................ | 260/248 |
| 3,268,474 A | | 8/1966 | Hardy et al. ................ | 260/248 |
| 3,270,016 A | | 8/1966 | Duennenberger et al. ... | 260/248 |
| 3,423,360 A | | 1/1969 | Huber et al. ................. | 260/47 |
| 4,619,956 A | | 10/1986 | Susi ............................ | 524/87 |
| 4,740,542 A | | 4/1988 | Susi ............................ | 524/87 |
| 5,084,570 A | | 1/1992 | Burdeska et al. ............ | 544/216 |
| 5,106,972 A | | 4/1992 | Burdeska et al. ............ | 544/219 |
| 5,288,778 A | | 2/1994 | Schmitter et al. ........... | 524/100 |
| 5,400,414 A | | 3/1995 | Thiele ......................... | 381/190 |
| 5,410,048 A | | 4/1995 | Leppard et al. ............. | 544/216 |
| 5,461,151 A | | 10/1995 | Waterman ................... | 544/216 |
| 5,476,937 A | | 12/1995 | Stevenson et al. .......... | 544/216 |
| 5,478,935 A | | 12/1995 | Reinehr et al. ............. | 544/180 |
| 5,489,503 A | | 2/1996 | Toan ........................... | 430/507 |
| 5,543,518 A | | 8/1996 | Stevenson et al. .......... | 544/215 |
| 5,545,836 A | | 8/1996 | Reinehr et al. ............. | 544/216 |
| 5,591,850 A | | 1/1997 | Birbaum et al. ............ | 544/216 |
| 5,597,854 A | | 1/1997 | Birbaum et al. ............ | 524/100 |
| 5,668,200 A | | 9/1997 | Valet et al. .................. | 524/100 |
| 5,686,233 A | | 11/1997 | Valet et al. .................. | 430/512 |
| 5,726,310 A | * | 3/1998 | Orban et al. ................ | 544/216 |

FOREIGN PATENT DOCUMENTS

| | | |
|---|---|---|
| CH | 480091 | 10/1969 |
| CH | 484695 | 1/1970 |
| EP | 0444323 | 9/1991 |
| EP | 0649841 | 10/1994 |
| GB | 1033387 | 6/1966 |
| JP | 60260502 | 12/1985 |
| JP | 09059263 | 3/1997 |

OTHER PUBLICATIONS

Brunetti H and Luthi CE, 1972, "Die synthese von aymmetrisch substituierten o–hydroxyphenyl–s–triazinen", Helv Chimica Acta 55:1566–1595.

Horikoshi Y et al., 1974, "Friedel–Crafts reactions of phenols with cyanuric chloride", Nippon Kagaku Kaishi, 3:530–535.

Tanimoto S and Yamagata M, 1995, "Composition of ultraviolet light absorbers having 2–(hydroxyphenyl)–1,3,5–triazine moiety as the functional group", Senryo To Yakahin (Dyestuffs and Chemicals) 40:325–339.

* cited by examiner

*Primary Examiner*—Richard L. Raymond
*Assistant Examiner*—Venkataraman Balasubramanian
(74) *Attorney, Agent, or Firm*—Tyler A. Stevenson

(57) ABSTRACT

The invention provides new processes for preparing compositions containing at least one triazine compound, including new compounds for use in these processes to form the compositions and the new compositions that are formed.

10 Claims, No Drawings

PROCESS FOR MAKING 2-HYDROXY-4-ALKOXYPHENYL OR 2,4-DIHYDROXYPHENYL SUBSTITUTED 1,3,5-TRIAZINE UV ABSORBERS

This application claims the benefit of U.S. Provisional Application No. 60/099,220. filed Sep. 4, 1998 and is a continuation of application Ser. No. 09/388,645, filed Sep. 2, 1999, now abandoned.

FIELD OF THE INVENTION

This invention relates to new processes for the preparation of substituted triazines which have utility as ultraviolet radiation absorbers.

BACKGROUND OF THE INVENTION

Exposure to sunlight and other sources of ultraviolet radiation is known to cause degradation of a wide variety of materials, especially polymeric materials. For example, polymeric materials such as plastics often discolor and/or become brittle as a result of prolonged exposure to ultraviolet light. Accordingly, a large body of art has been developed directed towards materials such as ultraviolet light absorbers and stabilizers which are capable of inhibiting such degradation.

A class of materials known to be ultraviolet light absorbers are triazines. Triazine ultraviolet light absorbers are a class of compounds which have at least one 2-hydroxyphenyl substituent on the 1,3,5-triazine ring.

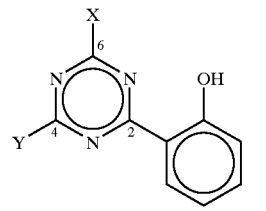

2-(2-Hydroxyphenyl)-1,3,5-triazines
X, Y = substituents

Trisaryltriazine ultraviolet light absorbers are compounds which have aromatic substituents at the 2-, 4- and 6 positions of the 1,3,5-triazine ring, and in which at least one of the aromatic rings has a hydroxyl substituent at the ortho position. These aromatic rings may contain other substituents or may be fused polyaromatics. In general this class of compounds is well known in the art. Disclosures of a number of such trisaryl-1,3,5-triazines, as well as processes for preparing and uses thereof, can be found in the following publications, all of which are incorporated by reference as if fully set forth herein: U.S. Pat. Nos. 3,118,887, 3,242,175, 3,244,708, 3,249,608, 3,268,474, 3,423,360, 4,619,956, 4,740,542, 5,084,570, 5,288,778, 5,461,151, 5,476,937, 5,478,935, 5,543,518, 5,545,836, 5,591,850, and 5,597,854, British patent 1,033,387, Swiss patents 480,091 and 484,695, European patent applications 0,444,323 and 0,649,841, and PCT applications WO94/05645, and WO96/28431.

A commonly used class of trisaryl-1,3,5-triazine ultraviolet light absorbers is based on 2-(2,4-dihydroxyphenyl)-4,6-bisaryl-1,3,5-triazines. In these compounds two non-phenolic aromatic groups and one phenolic aromatic group are attached to the 1,3,5-triazine. The phenolic aromatic group is derived from resorcinol.

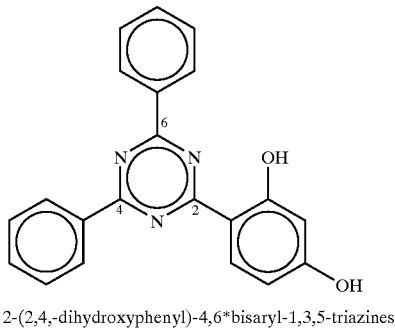

2-(2,4,-dihydroxyphenyl)-4,6*bisaryl-1,3,5-triazines

Of this class of compounds there are number of commercial products in which the para-hydroxyl group of the phenolic ring is functionalized and the non-phenolic aromatic rings are either unsubstituted phenyl (e.g., TINUVIN 1577) or m-xylyl (e.g., CYASORB UV-1164, CYASORB UV-1164L and TINUVIN 400). These 2-(2-hydroxy-4-alkoxyphenyl)-4,6-bisaryl-1,3,5-triazines UV absorbers exhibit high inherent light stability and permanence as compared to other classes of UV absorbers such as benzotriazoles and benzophenones.

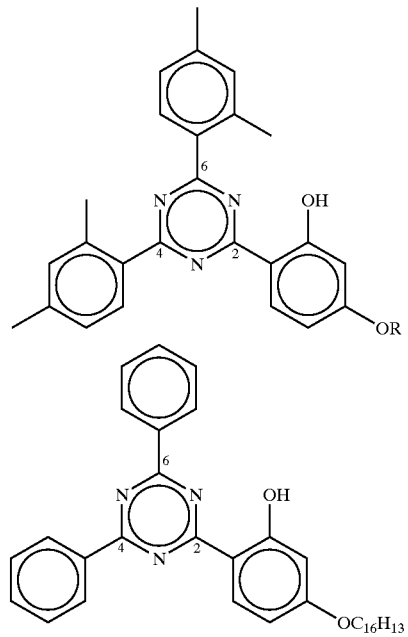

CYASORB UV 1164: R=n-$C_8H_{17}$    TINUVIN 1577

CYASORB UV 1164 (L): R=iso-$C_8H_{17}$

TINUVIN 400: R=$CH_2CH(OH)CH_2OC_NNH_{2N}$+1

N=12-14

These compounds are generally made by alkylating the corresponding 4-hydroxy precursor, viz., 2-(2,4-dihydroxyphenyl)-4,6-bisaryl-1,3,5-triazine with alkylating reagents.

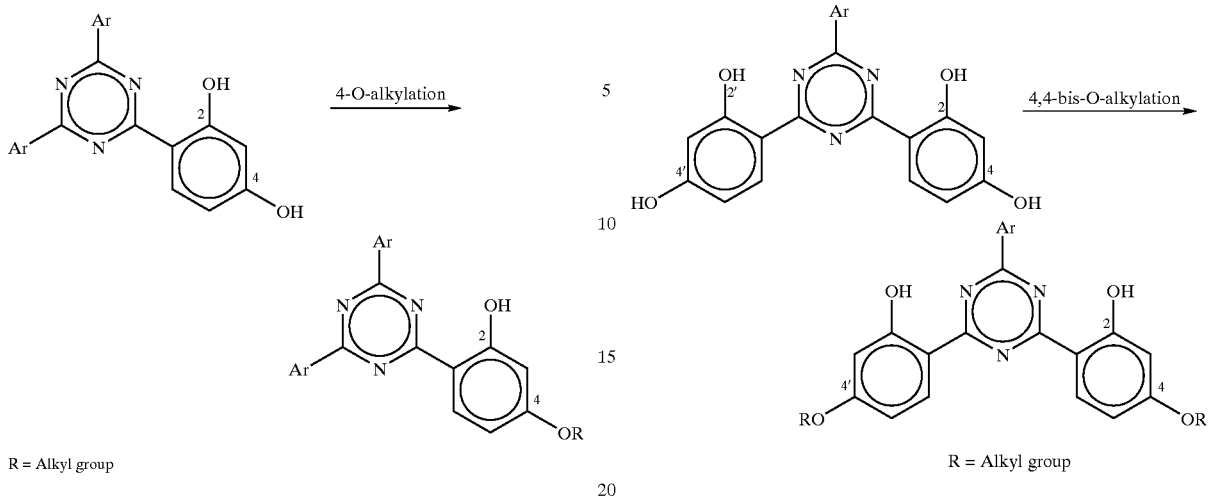

R = Alkyl group

For example, CYASORB UV-1164 is made by reacting 2-(2,4-dihydroxyphenyl)-4,6-bis(2,4-dimethylphenyl)-1,3,5-triazine with 1-octyl halide in the presence of a base.

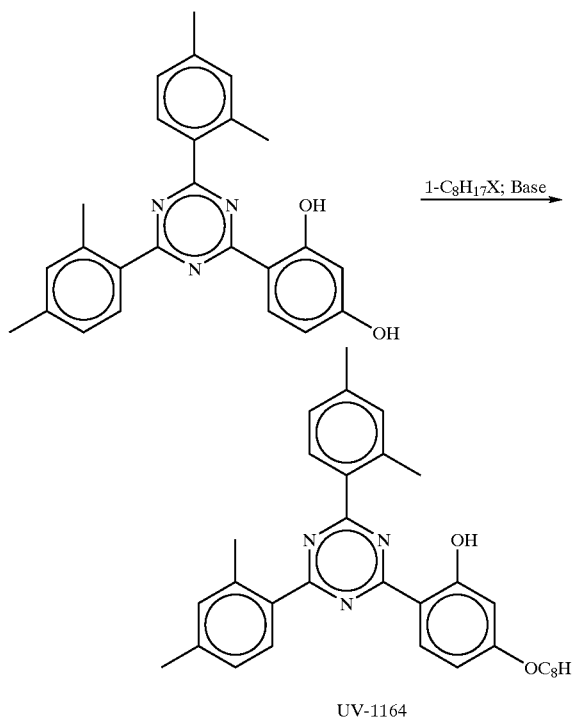

UV-1164

A second class of trisaryl-1,3,5-triazine ultraviolet light absorbers is based on 2,4-bis(2,4-dihydroxyphenyl)-6-aryl-1,3,5-triazines. In these compounds two resorcinol rings and one non-phenolic aromatic ring are attached to the 1,3,5-triazine, the 4 and 4' hydroxyl groups of the two resorcinol rings being further alkylated. Disclosures of such triazines and applications thereof, can be found in U.S. Pat. Nos. 5,489,503, 5,668,200 and 5,686,233, each of which is incorporated by reference as if fully set forth herein.

U.S. Pat. No. 5,668,200 discloses that the combination of the above two classes of triazine ultraviolet absorbers has some advantages over their use individually.

Several approaches are reported in the literature regarding methods of production of 2-(2,4-dihydroxyphenyl)-4,6-bisaryl-1,3,5-triazines and 2,4-bis(2,4-dihydroxyphenyl)-6-aryl-1,3,5-triazines, the precursors, respectively, to 2-(2-hydroxy-4-alkoxyphenyl)-4,6-bisaryl-1,3,5-triazines and 2,4-bis(2-hydroxy-4-alkoxyphenyl)-6-aryl-1,3,5-triazine ultraviolet absorbers. For example, H. Brunetti and C. E. Luethi, *Helvetica Chimica Acta,* vol. 55, pages 1566–1595 (1972), and S. Tanimoto and M. Yamagata, *Senryo to Yakahin,* vol. 40 (12), pages 325–339 (1995).

One widely used approach, shown below, involves the reaction of 2-chloro-4,6-bisaryl-1,3,5 triazines and 2,4-dichloro-6-aryl-1,3,5-triazines, respectively, with resorcinol in the presence of aluminum chloride to form the aforementioned mono- and bis- precursors. A disadvantage of this process is that it requires an additional alkylation step to form the 2-hydroxy-4-alkoxyphenyl product. The alkylation step has associated problems such as ease of reaction and selectivity.

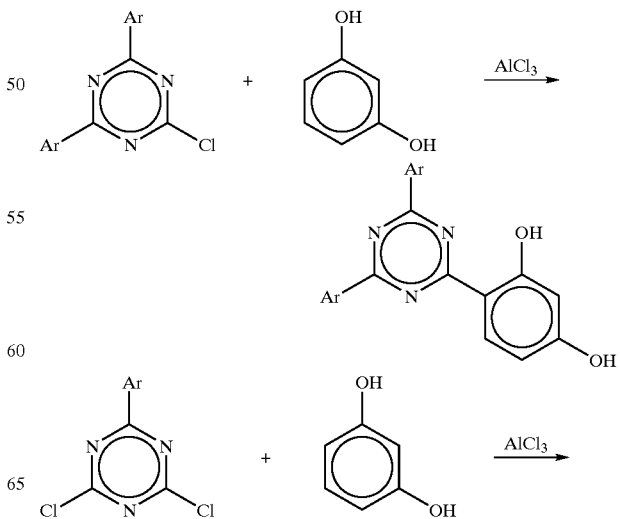

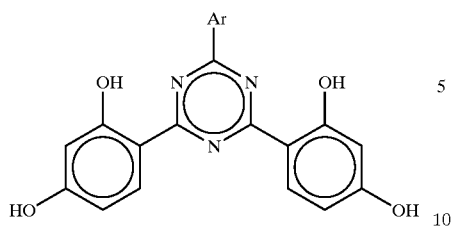

An alternate approach to the preparation of 2,4-bis(2,4-dihydroxyphenyl)-6-aryl-1,3,5-triazines involves the reaction of 2,4-bis(2,4-dihydroxyphenyl)-6-chloro-1,3,5-triazines with aromatic compounds in the presence of aluminum chloride.

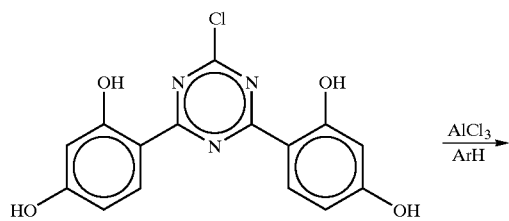

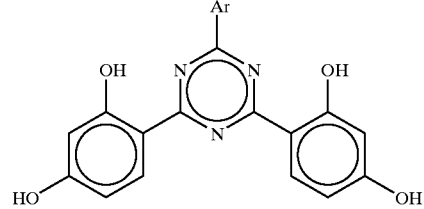

A third class of trisaryl-1,3,5-triazine ultraviolet light absorbers is based on 2,4,6-tris(2,4-dihydroxyphenyl)-1,3,5-triazines. In these compounds, all three aryl groups on the triazine ring are derived from resorcinol. Disclosures of such trisaryltriazines, and applications thereof, can be found in U.S. Pat. Nos. 3,268,474, 5,400,414 and 5,410,048, each of which is incorporated by reference as if fully set forth herein.

These compounds are generally prepared from cyanuric chloride in a two step process, shown below, wherein cyanuric chloride is first reacted with resorcinol to form 2,4,6-tris-(2,4-dihydroxyphenyl)-1,3,5-triazine, which is subsequently reacted with an alkylating agent in a second step to form the desired 2,4,6-tris-(2-hydroxy-4-alkoxyphenyl)-1,3,5-triazines product. For example, U.S. Pat. No. 3,268,474 discloses the reaction of cyanuric chloride with resorcinol to form 2,4,6-tris(2,4-dihydroxyphenyl)-1,3,5-triazine with no formation of carbon-oxygen linked products. This approach has disadvantages in that the solubility of 2,4,6-tris-(2,4-dihydroxyphenyl)-1,3,5-triazine in common organic solvents is poor, thus making the alkylation step difficult, and that side products due to overalkylation are also formed.

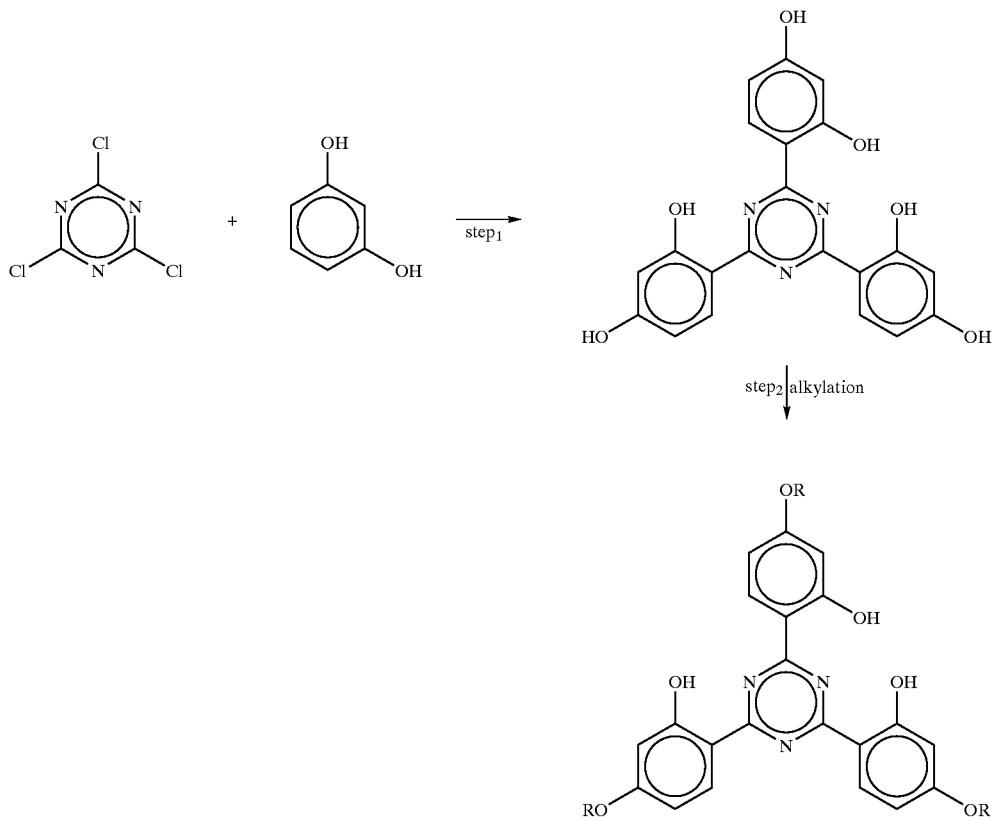

U.S. patent 3,268,474

Similarly, reaction of cyanuric chloride with dialkylated resorcinol is known in the art. For example, U.S. Pat. No. 3,268,474 discloses the reaction of cyanuric chloride with an excess of 1,3-dimethoxybenzene to form a mixture of 2,4,6-tris(2,4-dimethoxyphenyl)-1,3,5-triazine and 2,4-bis(2-hydroxy-4-methoxyphenyl)-6-(2,4-dimethoxyphenyl)-1,3,5-triazine.

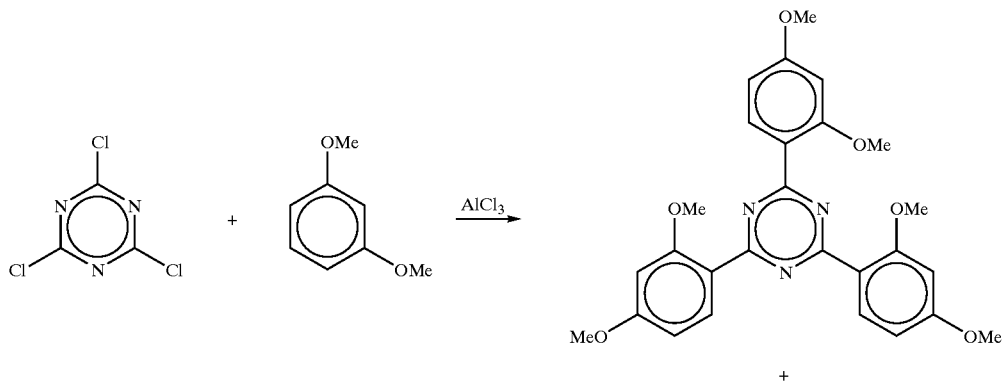

U.S. patent 3,268,474

In the reaction of cyanuric chloride with phenols, however, formation of either C-alkylation or O-alkylation has been reported depending on the substituents on the phenol. For example, Y. Horikoshi et al., *Nippon Kagaku Kaishi,* (3), pages 530–535, (1974), CA 81:152177. Japanese patent application 09–059,263 (CA 126: 277502) discloses the use of phenols substituted with alkyl, alkoxy, alkenyl, halo or nitro substituents to form carbon-oxygen products when reacted with cyanuric chloride.

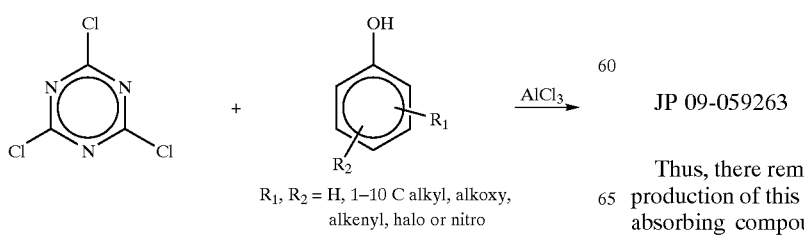

$R_1, R_2$ = H, 1–10 C alkyl, alkoxy, alkenyl, halo or nitro

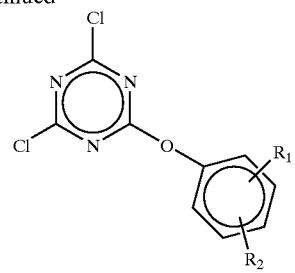

$R_1, R_2$ = H, 1–10 C alkyl, alkoxy alkenyl, halo or nitro

JP 09-059263

Thus, there remains a need for improved processes for the production of this class of important triazine ultraviolet light absorbing compounds, which processes avoid the need to carry out alkylation of intermediate products.

SUMMARY OF THE INVENTION

The present invention relates to new processes for the preparation of substituted triazines which have utility as ultraviolet radiation absorbers.

In particular, the present invention relates to a process for preparing a composition comprising at least one triazine compound of Formula A:

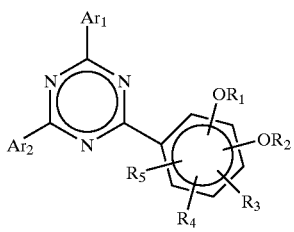

Formula A

In one embodiment, the invention relates to a process for preparing a composition comprising at least one triazine compound of Formula A, which process comprises reacting in the presence of a first catalyst, sufficient amounts of a compound of Formula D:

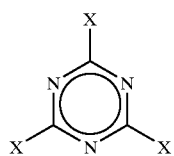

Formula D wherein X is a halogen, and a compound of Formula E:

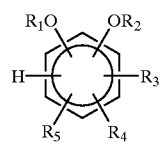

Formula E wherein $R_1$, $R_2$, $R_3$, $R_4$ and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R'are the same or different and each is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, optionally with either of $R_3$ and $R_4$, or $R_4$ and $R_5$, taken together being a part of a saturated or unsaturated fused carbocyclic ring optionally containing O, N or S atoms in the ring, and Y is a direct bond, O, NR", or SR", wherein R"is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms; at a suitable temperature and pressure in the presence of an inert solvent and for a time sufficient to form a second reaction mixture comprising the composition.

In another embodiment, the invention relates to a process for preparing a composition comprising at least one triazine compound of Formula A, which process comprises:

(i) reacting in the presence of a first catalyst, sufficient amounts of a compound of Formula D:

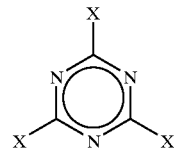

Formula D wherein X is a halogen, and a compound of Formula E:

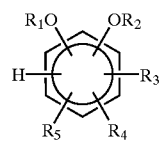

Formula E wherein $R_1$, $R_2$, $R_3$, $R_4$, and $R_5$ are as defined above, at a suitable temperature and pressure, and for a time sufficient to produce a first reaction mixture comprising at least one intermediate compound of:

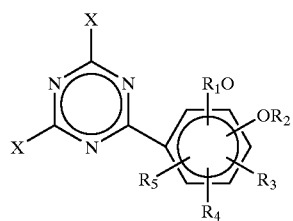

Formula I

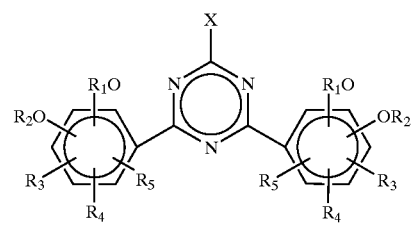

Formula J wherein $Ar_1$, X, $R_1$, $R_2$, $R_3$, $R_4$, and $R_5$ are as defined above; and (ii) reacting the first reaction mixture and a compound of Formula F:

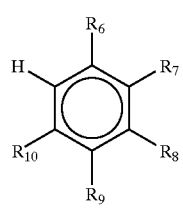

Formula F wherein $R_6$, $R_7$, $R_8$, $R_9$ and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, SO₂R, SO₃H, SO₃M, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, and optionally with either of $R_6$ and $R_7$ taken together, $R_7$ and $R_8$ taken together, $R_8$ and $R_9$ taken together, or $R_9$ and $R_{10}$ taken together being a art of a saturated or unsaturated fused carbocyclic ring optionally containing O, N or S atoms in the ring, in the presence of a second catalyst and at a suitable temperature and pressure, and for a time sufficient to produce a second reaction mixture comprising the composition.

In yet another embodiment the invention relates to novel processes for the preparation of substituted triazines wherein intermediate products produced in a first reaction mixture may be isolated. The intermediate compounds of Formula I and Formula J are novel triazine compounds:

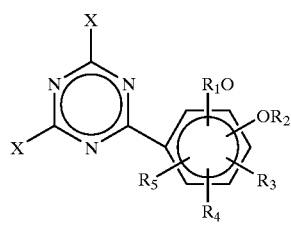

Formula I

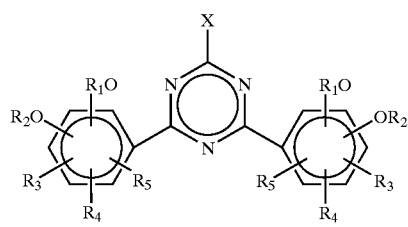

Formula J

DETAILED DESCRIPTION OF THE INVENTION

The present invention relates to new processes for the preparation of substituted triazines which have utility as ultraviolet radiation absorbers.

In particular, the present invention relates to a process for preparing a composition comprising at least one triazine compound of Formula A:

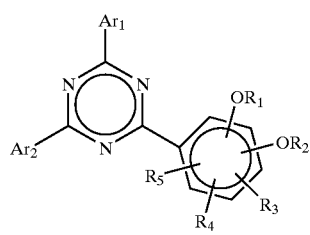

Formula A wherein $Ar_1$ and $Ar_2$ are the same or different, and each independently is a radical of a compound of Formula B:

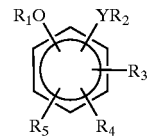

Formula B wherein $R_1$, $R_2$, $R_3$, $R_4$ and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms, OR, NRR', CONRR', OCOR, CN, SR, SO₂R, SO₃H, SO₃M, wherein M is an alkali metal, R and R' are the same or different and each is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, optionally with either of $R_3$ and $R_4$, or $R_4$ and $R_5$, taken together being a part of a saturated or unsaturated fused carbocyclic ring optionally containing O, N or S atoms in the ring, and Y is a direct bond, O, NR'', or SR'', wherein R'' is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms; or a radical of a compound of Formula C:

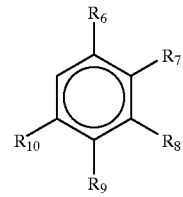

wherein $R_6$, $R_7$, $R_8$, $R_9$ and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, SO₂R, SO₃H, SO₃M, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, and optionally with either of $R_6$ and $R_7$ taken together, $R_7$ and $R_8$ taken together, $R_8$ and $R_9$ taken together, or $R_9$ and $R_{10}$ taken together being a part of a saturated or unsaturated fused carbocyclic ring optionally containing O, N or S atoms in the ring, which process comprises:

(i) reacting in the presence of a first catalyst, sufficient amounts of a compound of. Formula D:

Formula D

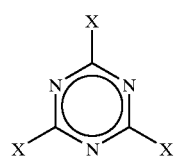

wherein X is a halogen, and a compound of Formula E:

Formula E

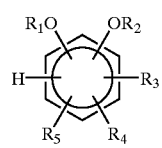

wherein $R_1$, $R_2$, $R_3$, $R_4$ and $R_5$ are as described above, at a suitable temperature and pressure in the presence of an inert solvent and for a time sufficient to form a second reaction mixture comprising the composition.

In one preferred embodiment, the process of the present invention relates to a process for preparing a composition comprising at least one triazine compound of Formula A:

Formula A

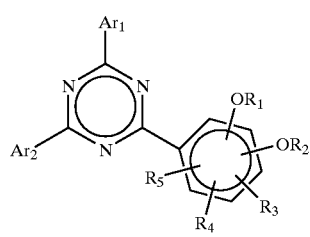

wherein $Ar_1$ and $Ar_2$ are the same or different, and each independently is a radical of a compound of Formula B:

Formula B

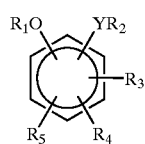

wherein Y, $R_1$, $R_2$, $R_3$, $R_4$ and $R_5$ are as described above or a radical of a compound of Formula C:

Formula C

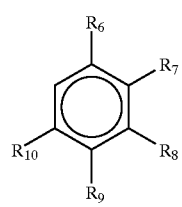

wherein $R_6$, $R_7$, $R_8$, $R_9$ and $R_{10}$ are as described above, which process comprises:

(i) reacting in the presence of a first catalyst, sufficient amounts of a compound of Formula D:

Formula D

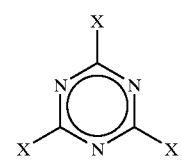

wherein X is a halogen, and a compound of Formula E:

Formula E

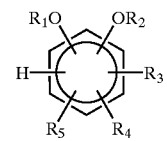

wherein $Ar_1$, X, $R_1$, $R_2$, $R_3$, $R_4$, and $R_5$ are as defined above at a suitable temperature and pressure, and for a time sufficient to produce a first reaction mixture comprising at least one intermediate compound of:

Formula I

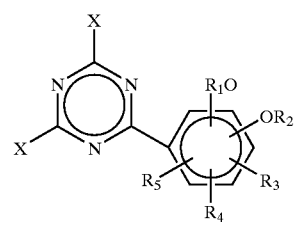

Formula J

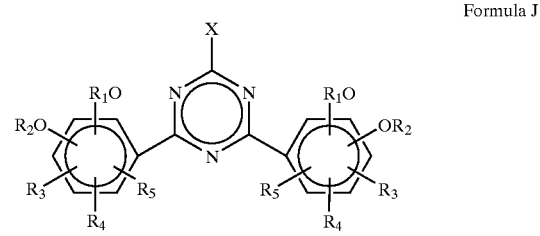

wherein $Ar_1$, X, $R_1$, $R_2$, $R_3$, $R_4$, and $R_5$ are as defined above; and (ii) reacting the first reaction mixture and a compound of Formula F:

Formula F

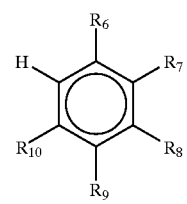

wherein $R_6$, $R_7$, $R_8$, $R_9$ and $R_{10}$ are as described above, in the presence of a second catalyst and at a suitable temperature and pressure, and for a time sufficient to produce a second reaction mixture comprising the composition.

In another preferred embodiment, the intermediate products produced in the first reaction mixture are isolated.

The intermediate compounds of Formula I and Formula J are novel triazine compounds:

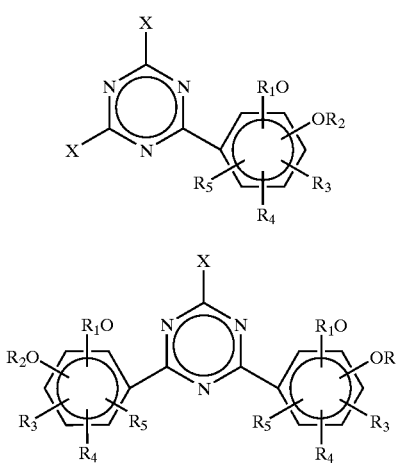

Formula I

Formula J

In another embodiment of the present invention, triazine compositions comprising Formula I, Formula J or mixtures therof may be further combined with a compound of Formula F or a compound of Formula E, as described above.

In another embodiment of the present invention, triazine compositions comprising Formula I, Formula J or mixtures therof are prepared.

The compound of Formula F may typically be selected from benzene, isopropylbenzene, di-isopropylbenzene, t-butyl benzene,toluene, ethylbenzene, ortho-xylene, meta-xylene, para-xylene, mesitylene, biphenyl, naphthalene, tetralin, substituted naphthalenes and substituted tetralins.

The reaction is carried out in a suitable solvent and at a temperature and pressure sufficient to produce a reaction mixture, and leads to production of a trisaryltriazine compound or mixture of trisaryltriazine compounds which have utility as ultraviolet radiation absorbers.

Suitable solvents for use in the process of the present invention are aliphatic hydrocarbons, hydrogenated aliphatic and aromatic compounds, aliphatic and aromatic nitro compounds and carbon disulfide. Preferred solvents are halogenated solvents such as chlorobenzene, dichlorobenzene and 1,1,2,2-tetrachloroethane.

The catalyst used in the process of the present invention is a Lewis Acid catalyst. Preferred catalysts are aluminum trihalides. The most preferred catalyst is aluminum trichloride.

The process of the present invention is carried out by combining the reactants in the reactor under suitable conditions to bringing about the reaction. The reaction takes place at a temperature of between about 0° C. to about 150° C. for a time of between about 1 to about 20 hours.

The amount of catalyst used is between about 0.5 to about 5 equivalents based upon the amount of the compound of Formula D.

The amount of compound of formula B used is between about 0.75 to 4 equivalents based upon the amount of the compound of Formula D.

Mode of Preparation

In a preferred embodiment of the reaction, cyanuric chloride is reacted with three equivalents of alkoxylated phenol in the presence of a Lewis Acid catalyst to produce 2,4,6-tris(2-hydroxy-4-alkoxyphenyl)-1,3,5-triazines as the major product.

From the literature, it would be expected that a carbon-oxygen linked product would result from the reaction of cyanuric chloride with partially alkoxylated resorcinol in the presence of a Lewis Acid. The formation of carbon-carbon inked products on reaction of cyanuric chloride with 3-alkoxyphenols is contrary to expectation.

Further, although two carbon-carbon linked products could result, one with the carbon-carbon linkage ortho to the phenolic hydroxyl and para to the alkoxy group, the other with the carbon-carbon linkage para to the phenolic hydroxyl and ortho to the alkoxy group, the former product with the carbon-carbon linkage ortho to the phenolic hydroxyl and para to the alkoxy group is preferably formed.

One-Step Process for the Preparation of 2,4,6-tris (2-hvdroxy-4-alkoxyphenyl)-1,3,5-triazine from cyanuric chloride

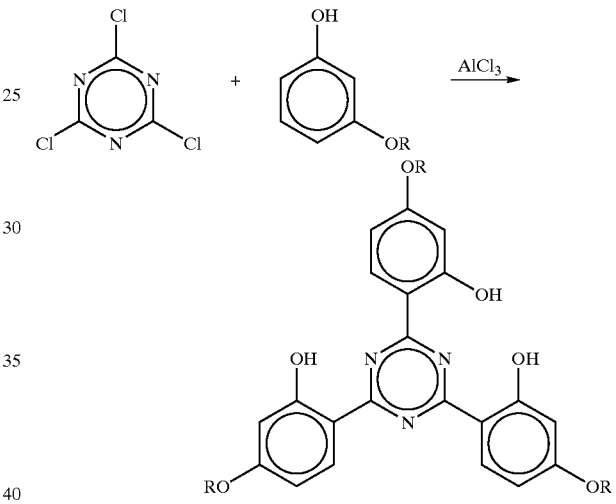

In another preferred embodiment of the present invention, cyanuric chloride is reacted with 1-2 equivalents of 3-alkoxyphenol in the presence of a Lewis Acid catalyst to produce a mixture of 2-(2-hydroxy-4alkoxyphenyl)-4,6-dichloro-1,3,5-triazines and/or 2,4-bis(2-hydroxy-4-alkoxyphenyl)-6-chloro-1,3,5-triazines, such mixtures being significantly free from 2,4,6-tris(2-hydroxy-4-alkoxyphenyl)-1,3,5-triazines. The reaction mixture can be further reacted with aromatic compounds, Z in the same pot to obtain a mixture of 2-(2-hydroxy-4alkoxyphenyl)-4,6-bisaryl-1,3,5-triazines and 2,4-bis(2-hydroxy-4-alkoxyphenyl)-6-aryl,1,3,5-triazines. Such mixtures are useful UV absorbers and are reported to be more effective than 2-(2-hydroxy-alkoxyphenyl)-4,6-bisaryl-1,3,5-triazines or 2,4-bis(2hydroxy-4-alkoxyphenyl)-6-aryl-1,3,5-triazines used individually. However, if desired, these mixtures can be separated at this state and the individual compound used separately. Furthermore the separation can be done following the initial step, and the pure intermediates then can be reacted with aromatics to obtain pure 2-(2-hydroxy-4alkoxyphenyl)-4,6-bisaryl-1,3,5-triazines or 2,4-bis(2-hydroxy-4-alkoxyphenyl)-6-aryl-1,3,5-triazines.

One-Pot Process for the the Preparation of a Mixture of 2-(2-hydroxy-4-alkoxyphenyl)-4,6-bisaryl-1,3,5-triazines and 2,4-bis(2-hydroxy-4-alkoxyphenyl)-6-aryl-1,3,5-triazines

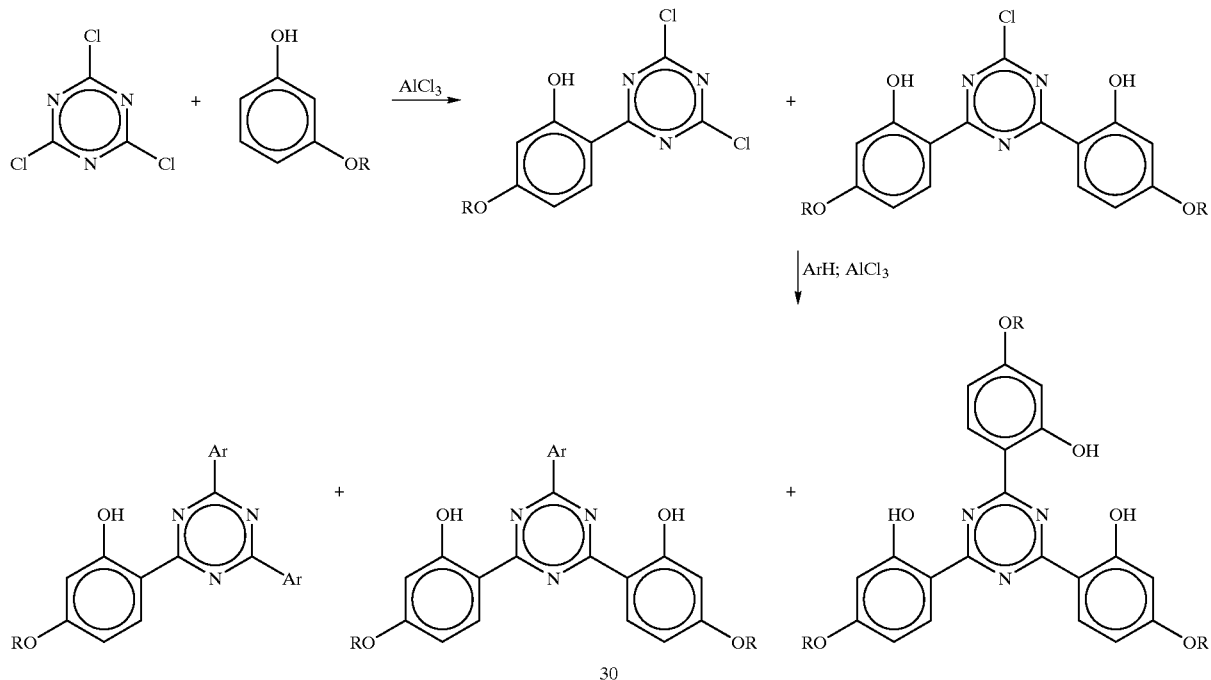

By changing the ratio of cyanuric chloride to 3-alkoxyphenol, it is also possible to get a mixture of mono-bis- and tris-triazines, namely, 2-(2-hydroxy-4-alkoxyphenyl)-4,6-bisaryl-1,3,5-triazines, 2,4-bis-(2-hydroxy-4-alkoxyphenyl)-6-aryl-1,3,5-triazines and 2,4,6-tris-(2-hydroxy-4-alkoxyphenyl)-1,3,5-triazines.

In another preferred embodiment of the present invention, cyanuric chloride is reacted with 1-2 equivalents of 1,3-dialkoxybenzene in the presence of a Lewis Acid catalyst, and the reaction mixture reacted in a second step with aromatic compounds, Z to produce a mixture of 2-(2-hydroxy-4-alkoxyphenyl)-4,6-bisaryl-1,3,5-triazines, 2,4-bis(2-hydroxy-4-alkoxyphenyl)-6-aryl-1,3,5-triazines and 2-(2-hydroxy-4-alkoxyphenyl)-4-(2,4-dialkoxyphenyl)-6-aryl-1,3,5-triazines.

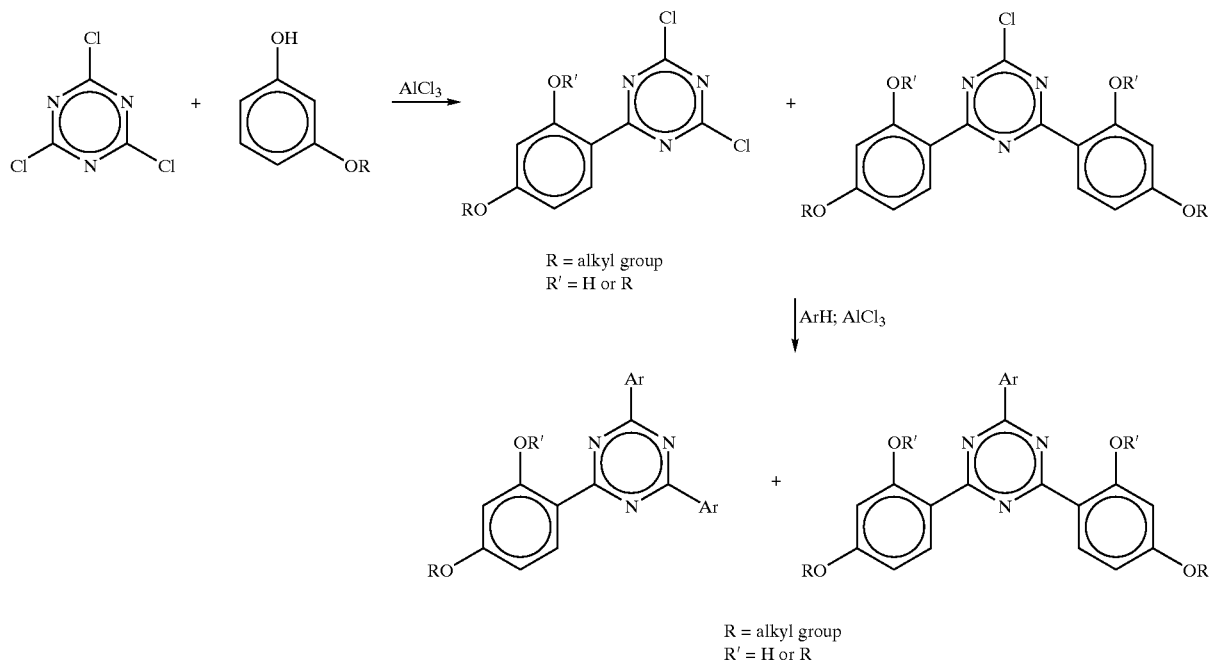

In another preferred embodiment of the present invention, cyanuric chloride is reacted with about 0.5 equivalents of resorcinol in the presence of a Lewis Acid catalyst to produce a mixture of mono- and bis-resorcinol substituted triazine products, 2-(2,4-dihydroxyphenyl)-4,6-dichloro-1,3,5-triazine and 2,4-bis(2,4-dihydroxyphenyl)-6-chloro-1,3,5-triazines. The reaction mixture on further reaction with aromatic compounds, Z produces a mixture of 2-(2,4-dihydroxyphenyl)-4,6-bisaryl-1,3,5-triazine and 2,4-bis(2,4-dihydroxyphenyl)-6-aryl-1,3,5-triazines.

One-Pot Process for the Preparation of a Combination of 2-(2.4-dihydroxyphenyl)-4,6-bisaryl-1,3,5-triazines and 2,4-bis(2.4-dihydroxyphenyl)-6-aryl-1,3,5-triazines -continued

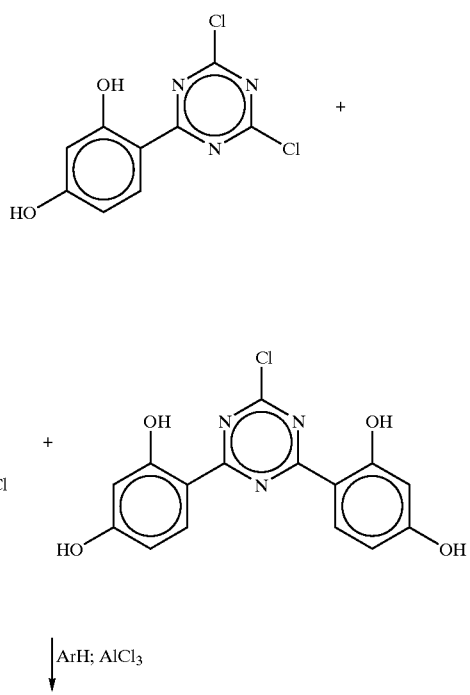

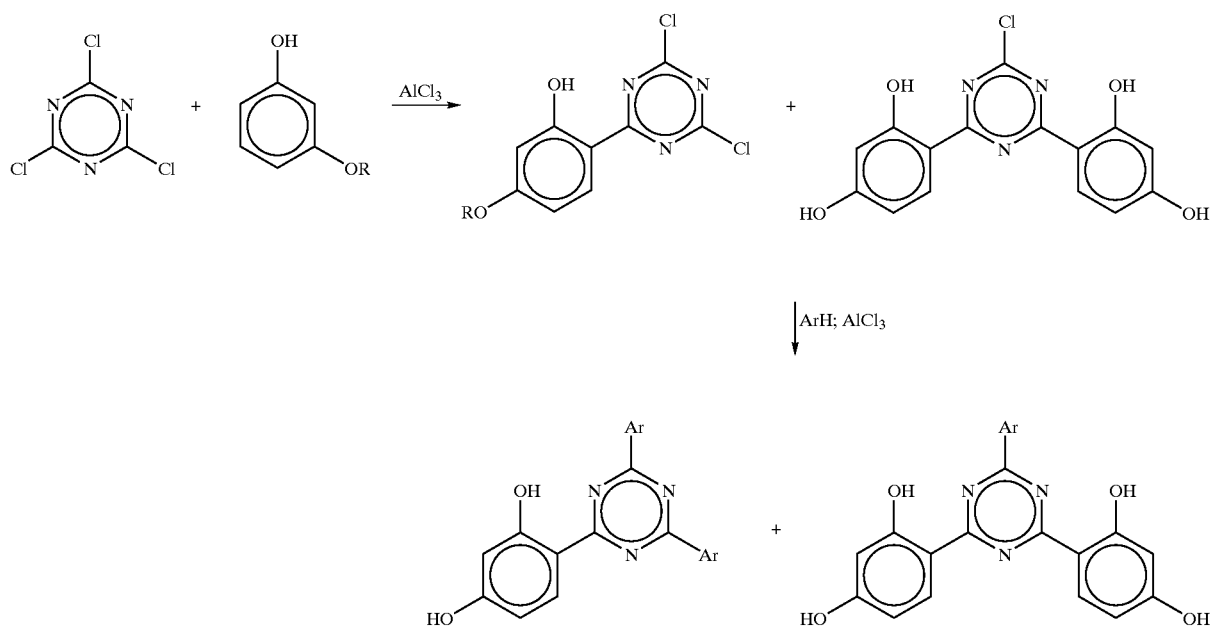

The 2-(2,4-dihydroxyphenyl)-4,6-dichloro-1,3,5-triazine and 2,4-bis(2,4-dihydroxyphenyl)-6-chloro-1,3,5-triazines formed from the reaction of cyanuric chloride with resorcinol can be separated at the first step. The reaction of 2-(2,4-dihydroxyphenyl)-4,6-dichloro-1,3,5-triazine thus obtained with aromatic compounds in the presence of a Lewis Acid catalyst produces 2-(2,4-dihydroxyphenyl)-4,6-bisaryl-1,3,5-triazines substantially free of 2,4-bis(2,4-dihydroxyphenyl)-6-aryl-1,3,5-triazines. This is a new and general process for making 2-(2,4-dihydroxyphenyl)-4,6-bisaryl-1,3,5-triazines.

-continued

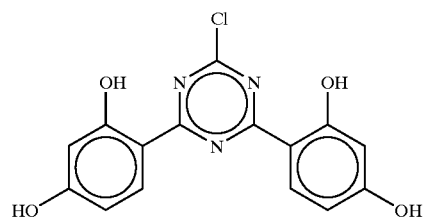

A new Two-step Process for the Preparation of 2-(2,4-dihydroxyphenyl)-46-bisaryl-1,3,5-triazines Step 1:

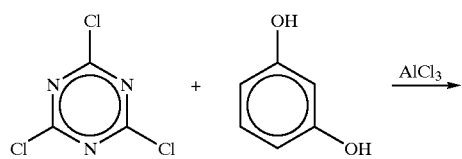

Step 2:

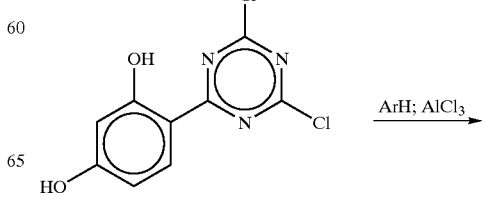

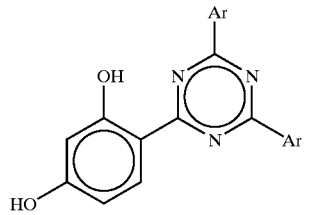

Uses of Triazines

The triazines of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

The triazines of the present invention can be employed to stabilize materials which are subject to degradation by ultraviolet radiation by incorporating the presently claimed compounds into polymeric materials, either chemically or physically. Non-limiting examples of polymeric materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfide, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

Further non-limiting examples of specific polymers which may be stabilized include:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).

2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.

3. Hydrocarbon resins (such as $C_5$-$C_9$) including hydrogenated modifications thereof and mixtures of polyalkylenes and starch.

4. Homo- and copolymers of styrenes such as styrene, p-methylstyrene and αa-methylstyrene.

5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.

6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.

7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.

8. Homo- and copolymers derived from α, β-unsaturated acids and derivatives thereof such as acrylic acid, methacrylic acid, acrylates, methacrylates, acrylamides and acrylonitriles.

9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.

10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.

For the preceding polymer groups 1-10, the present invention includes these polymers as prepared by metallocene catalysts.

11. Homo- and copolymers of cyclic ethers such as alkylene glycols and alkylene oxides, as well as copolymers with bisglycidyl ethers.
12. Polyacetals such as polyoxymethylene and those polyoxymethylenes which contain ethylene oxide as a comonomer; and polyoxymethylenes modified with thermoplastic polyurethanes, acrylates and/or MBS.
13. Polyphenylene oxides and sulfides.
14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.
15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).
16. Polyureas, polyimides, polyamide-imides, polyetherimides, polyesterimides, polyhydantoins and polybenzimidazoles.
17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; and also polyesters modified with polycarbonate or MBS.
18. Polycarbonates and polyester carbonates.
19. Polysulfones, polyether sulfones and polyether ketones.
20. Crosslinked polymers derived from aldehydes condensation resins such as phenol/formaldehyde resins, urea/formaldehyde resins and melamine/formaldehyde resins.
21. Drying and non-drying alkyd resins.
22. Unsaturated polyester resins derived from copolyesters of saturated and unsaturated dicarboxylic acids with polyhydric alcohols and vinyl compounds as crosslinking agents and also halogen-containing modifications thereof.
23. Crosslinkable acrylic resins derived from substituted acrylates such as epoxy acrylates, hydroxy acrylates, isocyanato acrylates, urethane acrylates or polyester acrylates.
24. Alkyd resins, polyester resins and acrylate resins crosslinked with melamine resins, urea resins, isocyanates, isocyanurates, carbamates or epoxy resins.
25. Crosslinked epoxy resins derived from aliphatic, cycloaliphatic, heterocyclic and/or aromatic glycidyl compounds such as bisphenol A and bisphenol F, which are crosslinked with customary hardeners such as anhydrides or amines.
26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers or oligomers and a polyunsaturated aliphatic oligomer.
32. Epoxymelamine resins such as light-stable epoxy resins cross-linked by an epoxy functional coetherified high solids melamine resin.

Other materials which can be stabilized include, for example:

33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.
38. Photographic film paper.
39. Ink.

The invention will now be illustrated by the following examples. The examples are not intended to be limiting of the scope of the present invention. In conjunction with the general and detailed descriptions above, the examples provide further understanding of the present invention.

EXAMPLES

Example 1

Reaction of Cyanuric Chloride with Resorcinol Isolation of 2-(2.4- dihydroxyphenyl)-4.6-dichloro-1,3,5-triazine and 2.4-bis(2.4-dihydroxyphenyl)-6-chloro-1,3,5-triazine To a stirring mixture of cyanuric chloride (1.84 g) and resorcinol (1,3-dihydroxybenzene; 0.55 g) in 25 mL of chlorobenzene was added aluminum chloride (0.7 g). The reaction mixture was stirred first at room temperature for 2 hr and then at 30° C. for 3 hr. The reaction mixture was cooled to room temperature and stirred at room temperature for 20 hr. To the mixture was then added 5 mL of chlorobenzene and the soluble portion was decanted and treated with aqueous dilute HCl to give a precipitate which was filtered, washed with water and dried. It was identified by mass and TLC to contain mainly 2-(2,4-dihydroxyphenyl)-4,6-dichloro-1,3,5-triazine. The insoluble portion of the reaction mixture was treated with aqueous dilute HCl separately to give a precipitate which was filtered, washed with water and dried to give a product identified by mass and TLC to contain mainly 2,4-bis(2,4-dihydroxyphenyl)-6-chloro-1,3,5-triazine. 2-(2,4-dihydroxyphenyl)-4,6-dichloro-1,3,5-triazine and 2,4-bis(2,3-dihydroxyphenyl)-6-chloro-1,3,5-triazine was formed in roughly equal amounts.

Example 2

Preparation of 2-(2.4-dihydroxyphenyl)-4.6-bis(2.4-dimethylphenyl)-1,3,5-triazine To a stirring solution of 2-(2,4-dihydroxyphenyl)-4,6-dichloro-1,3,5-triazine (257 mg) in 5 mL of m-xylene was added aluminum chloride (200 mg). The reaction mixture was stirred at room temperature for 24 hr. The reaction mixture was analyzed by TLC after usual work-up to contain mainly one product which was identical with 2-(2,4-dihydroxyphenyl)-4,6-bis(2,4-dimethylphenyl)-1,3,5-triazine.

Example 3

Reaction of Cyanuric Chloride with Resorcinol Followed by m-xylene: One-pot Preparation of a Combination of 2-(2.4-dihydroxyphenyl)-4.6-bis (2.4-dimethylphenyl)-1,3.5-triazine and 2,4-bis(2,4-dihydroxylphenyl)-6-(2,4-dimethylphenyl)-1,3,5-triazine.

The reaction of cyanuric chloride with resorcinol was repeated following the procedure described in Example 1, with the exception that the crude mixture was not worked up, but further treated with m-xylene in the same pot. The formation of a combination of products 2-(2,4-dihydroxyphenyl)-4,6-bis(2,4-dimethylphenyl)-1,3,5-triazine and 2,4-bis(2,4-dihydroxyphenyl)-6-(2,4-dimethylphenyl)-1,3,5-triazine was confirmed by HPLC analysis.

Example 4

Preparation of 2.4-Dichloro-6-(2,4-dioctyloxy)-1,3,5-triazine

To a stirred mixture of 0.92 g cyanuric chloride (5 mmol) and 1.67 g of 1,3-dioctyloxybenzene in 12 mL of chlorobenzene at room temperature under nitrogen was added 0.67 g of aluminum trichloride. The mixture was heated at 30° C. for 4 hr. HPLC analysis indicated complete consumption of the 1,3-dioctyloxybenzene. The reaction mixture was slowly poured into a vigorously stirred mixture of 100 mL 5% aq. hydrochloric acid, ice, and water (total volume 300 mL), and methylene chloride was used to rinse the reaction flask. All solids dissolved upon stirring. The organic layer was washed with deionized water and the solvents removed in vacuo on a rotary evaporator, first at room temperature, and then at 50° C. to give a yellow oil. The formation of the title compound (MH$^+$ m/e=482) along with 2-chloro-4,6-bis-(2,4-dioctyloxyphenyl)-1,3,5-triazine (MH$^+$ml/e=780) in a 92:8 ratio (MS peak intensity ratios), respectively, was confirmed by thermal spray MS. The identity of 2,4-dichloro-6-(2,4-dioctyloxyphenyl)-1,3,5-triazine was further established by its chemical transformation to 2-(2-hydroxy-4-octyloxy)-4,6-bis(2,4-dimethylphenyl)-1,3,5-triazine. See Example 5.

Example 5

Preparation of 2-(2-Hydroxy-4-Octyloxy)-4,6-bis(2,4-dimethylphenyl)-1,3,5-triazine from 2,4-Dichloro-6-(2,4-dioctyloxphenyl)-1,3,5-triazine To a stirred mixture of 0.72 g of 2,4-dichloro-6-(2,4-dioctyloxyphenyl)-1,3,5-triazine (as prepared in Example 4), 5 mL of m-xylene and 5 mL of chlorobenzene at room temperature under nitrogen was added 0.40 g of aluminum trichloride. The mixture was heated at 60° C. for 3.5 hr. At this point a sample was drowned in 5% aq. HCl and ice water, and extracted with ethyl acetate. HPL analysis showed the presence of 2-(2-hydroxy-4-octyloxy)-4,6-bis(2,4-dimethylphenyl)-1,3,5-triazine, which was established by comparison of the UV spectrum and retention time to a commercial sample of CYCOMB® UV-1164.

Example 6

One-pot Preparation of 2,4-Bis(2,4-dimethylphenyl)-6-(2-hydroxy-4-methoxy)-1,3,5-triazine from Cyanuric Chloride To a stirred mixture of 1.84 g cyanuric chloride (10 mmol) and 1.24 g of 3-methoxyphenol in 25 mL of ortho-dichlorobenzene at room temperature under nitrogen was added 3.44 g of aluminum trichloride. Ten min. after the addition, there was a brief exotherm to 28° C. The mixture was then stirred at 20–23° C. After 7.5 hr, 5 mL of m-xylene was added, and the solution was stirred for an additional 9 hr. at 20–23° C. At this point a sample was drowned in 5% aq. HCl and ice water, and extracted with ethyl acetate. HPLC analysis showed the presence of 2-(2-hydroxy-4-methoxy)-4,6-bis(2,4-dimethylphenyl)-1,3,5-triazine, which was confirmed by thermal spray MS (MH$^+$ ml/e=412) and UV spectroscopy ($\lambda_{max}$291,336 nm).

Example 7

Direct Preparation of 2.4.6-Tris(2-hydroxy-4-octyloxy)-1,3,5-triazine from Cyanuric Chloride To a stirring mixture of 0.615 g of cyanuric chloride, 2.22 g of resorcinol monooctyl ether in 25 mL chlorobenzene was gradually added with stirring 1.1 g of aluminum trichloride. The reaction mixture was stirred at room temperature for 2 hours and then gradually heated to 80° C., and was held at this temperature for 5 hours. The reaction mixture was allowed to cool to room temperature, and then quenched with ice-cold 2% aq. HCl. The reaction mixture was extracted with methylene chloride, methylene chloride extract washed with water, dried over anhydrous sodium sulfate, and concentrated under reduced pressure to give a residue containing the 2,4,6-Tris(2-hydroxy-4-octyloxy)-1,3,5-triazine as a product characterized by a direct comparison with a commercial sample of 2,4,6-Tris(2-hydroxy-4-octyloxy)-1,3,5-triazine on TLC and HPLC.

What is claimed is:

1. A process for preparing a triazine compound of the formula

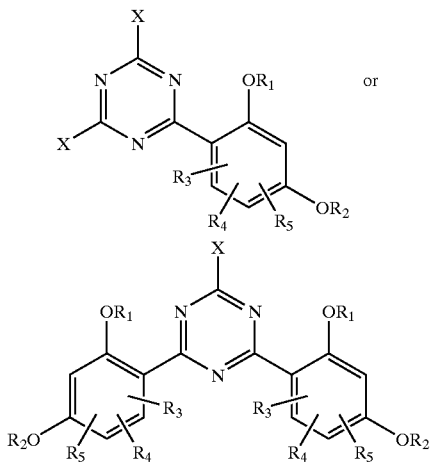

which process comprises (i) reacting in the presence of a first catalyst, sufficient amounts of a compound of formula (D)

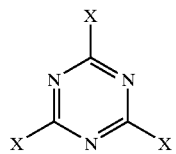

(D)

and a compound of formula (E)

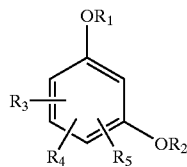

(E)

at a suitable temperature and pressure in the presence of a solvent and for a sufficient time, wherein X is a halogen, $R_1$ is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms, $R_2$ is alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms, $R_3$, $R_4$ and $R_5$ are the same or different and each is hydrogen, halogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms, OR, CONRR', OCOR, CN, SR; or $R_3$ and $R_4$, or $R_4$ and $R_5$, together form a saturated or unsaturated fused carbocyclic ring optionally containing O, N or S atoms in the ring, R and R' are the same or different and each is hydrogen, alkyl of 1 to 24 carbon atoms, alkenyl of 2 to 24 carbon atoms, acyl of 1 to 24.carbon atoms, aryl of 6 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms.

2. The process of claim 1 wherein the first catalyst is a Lewis acid and X is chlorine.

3. The process of claim 2 wherein the first catalyst is selected from the group consisting of aluminum tribromide, zinc chloride, boron trichloride, titanium tetrachloride, aluminum trichloride, and a mixture thereof.

4. The process of claim 1 the amount of catalyst is from about 0.5 to about 5 equivalents based upon the amount of the compound of formula (D).

5. The process of claim 1 wherein the amount of the compound of formula (E) is from about 0.75 to about 4 equivalents based upon the amount of the compound of formula (D).

6. The process of claim 5 wherein the amount of the compound of formula (E) is from about 1 to about 3 equivalents based upon the amount of the compound of formula (D).

7. (new) The process of claim 6 wherein the compound of formula (E) and the compound of formula (D) are reacted at a temperature of between about 0° C. and about 150° C.

8. The process of claim 7 wherein the compound of formula (E) and the compound of formula (D) are reacted at a temperature of between about 30° C. and about 100° C.

9. The process of claim 7 wherein the reaction of the compound of formula (E) and the compound of formula (D) is conducted in a halogenated solvent.

10. The process of claim 9 wherein the halogenated solvent is selected from the group consisting of chlorobenzene, dichlorobenzene, 1,1,2,2-tetrachloroethane, and mixtures thereof.

* * * * *